United States Patent
Shin et al.

(10) Patent No.: US 10,245,339 B2
(45) Date of Patent: Apr. 2, 2019

(54) APPARATUS AND METHOD OF STERILIZING LUMENS IN MEDICAL INSTRUMENTS

(71) Applicant: Webb Medical LLC, Philadelphia, PA (US)

(72) Inventors: Daniel Hyun Shin, Los Angeles, CA (US); Steven B. Krupnick, Philadelphia, PA (US); Casey Clark, Philadelphia, PA (US)

( * ) Notice: Subject to any disclaimer, the term of this patent is extended or adjusted under 35 U.S.C. 154(b) by 140 days.

(21) Appl. No.: 15/391,041

(22) Filed: Dec. 27, 2016

(65) Prior Publication Data

US 2017/0182194 A1 Jun. 29, 2017

Related U.S. Application Data

(60) Provisional application No. 62/272,263, filed on Dec. 29, 2015.

(51) Int. Cl.
| | |
|---|---|
| *A61L 2/00* | (2006.01) |
| *A61B 1/00* | (2006.01) |
| *G01N 23/00* | (2006.01) |
| *A61L 2/10* | (2006.01) |
| *A61B 1/12* | (2006.01) |
| *A61B 90/70* | (2016.01) |
| *A61B 1/012* | (2006.01) |

(52) U.S. Cl.
CPC .............. *A61L 2/10* (2013.01); *A61B 1/121* (2013.01); *A61B 90/70* (2016.02); *A61B 1/012* (2013.01); *A61B 2090/701* (2016.02); *A61L 2202/11* (2013.01); *A61L 2202/24* (2013.01)

(58) Field of Classification Search
CPC ....... A61L 2/10; A61L 2202/24; A61B 1/121; A61B 90/70
USPC ........ 422/1, 24; 250/455.11, 492.1; 600/133
See application file for complete search history.

(56) References Cited

U.S. PATENT DOCUMENTS

| | | | | |
|---|---|---|---|---|
| 5,439,595 | A | * 8/1995 | Downey, Jr. | ............... A61L 2/10 210/748.07 |
| 2006/0104859 | A1 * | 5/2006 | Tribelsky | ............... A23B 7/015 422/24 |
| 2009/0252467 | A1 * | 10/2009 | Okuno | ................ H01S 3/06795 385/122 |

(Continued)

OTHER PUBLICATIONS

Applicant Admitted Prior Art (specification, pp. 2-3) (Year: 2015).*

*Primary Examiner* — Monzer R Chorbaji
(74) *Attorney, Agent, or Firm* — Caesar Rivise, PC

(57) ABSTRACT

Disclosed are apparatus and a method for sterilizing an internal surface of a lumen in a medical instrument, e.g., an endoscope. The apparatus is in the form of an elongated UVC light guide, e.g., an optic fiber, having a central longitudinal axis and which is configured to be extended down the lumen in the instrument, and a housing including a source of UVC light. The UVC light guide includes a distal end portion and is configured to carry UVC light internally from the source of UVC light to the distal end portion. The distal end portion includes a reflective surface for directing the UVC light radially outward with respect to the central longitudinal axis, whereupon when the UVC light guide is extended into the lumen in the medical instrument the radially directed UVC light impinges the internal surface of the lumen to sterilize it.

25 Claims, 1 Drawing Sheet

(56) References Cited

U.S. PATENT DOCUMENTS

2014/0271348 A1\* 9/2014 Deal .................... A61L 2/00
422/3

\* cited by examiner

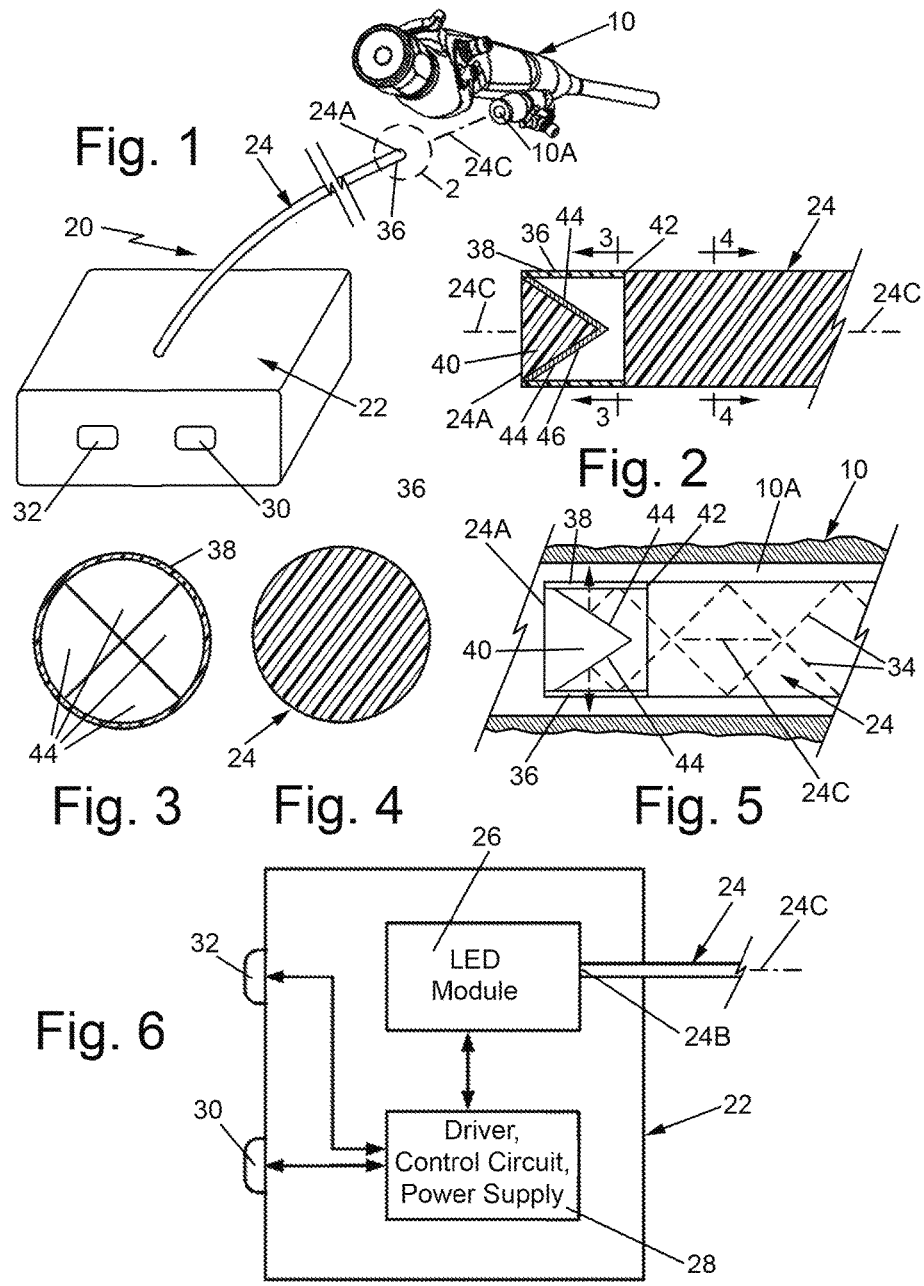

APPARATUS AND METHOD OF STERILIZING LUMENS IN MEDICAL INSTRUMENTS

CROSS-REFERENCE TO RELATED APPLICATIONS

This utility application claims the benefit under 35 U.S.C. § 119(e) of Provisional Application Ser. No. 62/272,263 filed on Dec. 29, 2015, entitled Apparatus and Method of Sterilizing Lumens in Medical Instruments. The entire disclosure of this provisional application is incorporated by reference herein.

FIELD OF THE INVENTION

This invention relates generally to sterilizing apparatus and more particularly to apparatus and methods of sterilizing lumens in medical instruments, such as endoscopes.

BACKGROUND OF THE INVENTION

As is known, endoscopes are rigid or flexible medical devices that allow for visualization of the inside of the body of a patient. In particular, one common use of an endoscope is to access some interior target in the patient's body through a natural orifice, e.g., the mouth, anus, urethra, etc. Typically, the endoscope includes a digital or fiber optic/camera system to transmit the image of the target onto an externally located video monitor. A light is commonly provided on the distal end or tip of the endoscope to illuminate the target. One feature that greatly increases the utility of the endoscope is a "working channel", which is a narrow passageway or lumen that runs the length of the endoscope, and through which various medical devices can be inserted into the patient's body to perform various medical procedures in the sinus cavities, upper and lower gastrointestinal tracts, lung fields, larynx, and intra-abdominal spaces, etc.

A universal feature of natural body orifices is the fact that these areas are colonized with bacteria. This is often described as bacterial "colonization." These bacteria may be harmful if passed from patient to patient. Among the regions in the endoscope that are most susceptible to bacterial colonization is the working channel. Thus the endoscope and its working channel must undergo a cleaning or sterilization process in between uses. This process typically involves brushing as well as a chemical bath. Notwithstanding the widespread use of such sterilization techniques, there are numerous documented cases of transmission of dangerous bacteria between patients via endoscopes. That fact underscores the need for a more effective and reliable method and apparatus for sterilizing lumens in endoscopes and other medical instruments.

Ultraviolet C (UVC) light is known for its germicidal properties. In U.S. Published Patent Application 2014/0271348 (Deal et al.) there is disclosed a disinfector which makes use of UVC light to disinfect a medical device having channels therein, such as an endoscope. That disinfector is in the form of a cabinet that includes a sterilization chamber having highly UVC reflective interior surfaces into which the instrument to be sterilized is placed. A plurality of UVC emitters or lamps is provided to maximize the dispersion of the reflected UVC light within the sterilization chamber. A plurality of UVC sensors is positioned in the chamber and located so as to only measure reflected UVC light. A microcontroller system reads the UVC sensors to determine when all the exterior surfaces of the instrument have been exposed to a desired UVC dosage to sterilize those surfaces. In order to sterilize internal lumens in the instrument, the disinfector is provided with a cable for introduction into the lumen to be sterilized. The cable has one or more UVC emitters, e.g., light emitting diodes (LEDs), located at the end of the cable or positioned along the cable. A UVC sensor is also provided on the cable. The cable is inserted through interior channel to be sterilized to transport the emitter(s) and the sensor through the interior channel, and to provide current to the LED(s) and the sensor. The UVC light emitted serves to sterilize the lumen as the cable is moved through it. The sensor provides a signal indicative of the UVC light dosage received, which signal is used by an associated microcontroller system for controlling movement of the cable through the lumen.

While the aforementioned published application discloses apparatus which appears to address several needs of the prior art, it nevertheless leaves much to be desired from several standpoints, e.g., simplicity of construction, cost, and ease and speed of use. Thus a need still exists for apparatus and method for sterilizing a lumen in a medical instrument which is simple in construction, relatively low in cost, is easy to use, and is effective for quickly sterilizing the lumen. The subject invention addresses those needs.

SUMMARY OF THE INVENTION

In accordance with one aspect of this invention there is provided an apparatus for sterilizing the internal surface of a lumen in a medical instrument. The apparatus basically comprises an elongated UVC light guide, e.g., an optic fiber, having a central longitudinal axis. The UVC light guide is configured to be extended down the lumen in the instrument and includes a distal end portion and a proximal end portion. The proximal end portion is configured to be coupled to a source of UVC light. The source of UVC light includes at least one LED for producing UVC light suitable for sterilizing the internal surface of the lumen when the at least one LED is energized, whereupon the UVC light is carried internally by the UVC light guide from the source of UVC light to the distal end portion of the UVC light guide. The distal end portion of the UVC light guide is configured for directing the UVC light radially outward from the central longitudinal axis, whereupon when the UVC light guide is extended into the lumen in the medical instrument, the radially directed UVC light impinges the internal surface of the lumen to sterilize it.

In accordance with one preferred aspect of this invention, the UVC light guide includes a distal end, wherein the distal end portion comprises a reflective attachment secured to the distal end of the optic fiber and is configured to direct the UVC light radially outward from the central longitudinal axis.

In accordance with another preferred aspect of this invention, the UVC light guide comprises an optic fiber, which may be either a single optic fiber or an optic fiber bundle.

In accordance with another preferred aspect of this invention, the UVC light guide comprises a liquid light guide or a holey photonic crystal fiber or a hollow photonic crystal fiber.

In accordance with another preferred aspect of this invention, the apparatus comprises the source of UVC light.

In accordance with another preferred aspect of this invention, the source of UVC light is located within a housing, and wherein the housing includes an actuator to control the operation of the UVC light source and an indicator to indicate when the UVC light source is providing the UVC light into the fiber optic.

In accordance with another aspect of this invention, a method of sterilizing the internal surface of a lumen in a medical instrument is provided. The method entails providing an apparatus including a source of UVC light and an elongated UVC light guide having a central longitudinal axis, a distal end portion and a proximal end portion. The source of UVC light includes at least one LED for producing UVC light suitable for sterilizing the internal surface of the lumen when the at least one LED is energized. The distal end portion of the UVC light guide is configured for directing UVC light radially outward from the central longitudinal axis. The source of UVC light is coupled to the UVC light guide. The UVC light guide is inserted within the lumen of the instrument and the source of UVC light is caused to produce UVC light, whereupon the UVC light guide carries the UVC light from the source internally down the UVC light guide to the distal end portion from whence the UVC light is directed radially outward to impinge the internal surface of the lumen to sterilize that surface. The UVC light guide is moved through the lumen while the source of UVC light is producing the UVC light to thereby sterilize the length of the internal surface of the lumen.

BRIEF DESCRIPTION OF THE DRAWING FIGURES

FIG. 1 is an isometric view of one exemplary apparatus constructed in accordance with this invention for sterilizing a lumen in a medical instrument, e.g., an endoscope;

FIG. 2 is an enlarged longitudinal cross-sectional view of the distal tip of the apparatus shown within the broken circle designed with the reference number 2 in FIG. 1;

FIG. 3 is a sectional view taken along line 3-3 of FIG. 2;

FIG. 4 is a sectional view taken along line 4-4 of FIG. 2;

FIG. 5 is an enlarged illustration showing the path of the UV light through the distal end of the apparatus of FIG. 1; and FIG. 6 is a block diagram of the components making up a portion of the apparatus shown in FIG. 1.

DETAILED DESCRIPTION OF THE PREFERRED EMBODIMENTS

Referring now to the drawings wherein like characters refer to like parts, there is shown in FIG. 1 an exemplary embodiment of an apparatus 20 for sterilizing the internal surface of the working channel or lumen 10A of an endoscope 10. The apparatus 20 basically comprises a housing 22 and an elongated UVC light guide 24.

As best seen in FIG. 6, the housing 22 includes a source 26 of UVC light. In the exemplary embodiment shown the source 26 is in the form of a module including one or more light emitting diodes (LEDs) configured for producing UVC light having a wavelength of from approximately 200-280 nm. Depending upon the construction of the LED(s), the power of each LED can be in the range of approximately less than 1 mW to more than 100 mW. One particularly suitable module 26 for producing UVC light of sufficient intensity to sterilize a surface to which the UVC light is directed in a short amount of time suitable for use in this invention is available from LG Innotek under the model designation LEUVA66G00HF00. The UVC source 26 is electrically connected to electrical circuitry 28 including a driver, a control circuit and a power supply. The driver, control and power supply circuitry 28 can be of any suitable construction, and is preferably configured to provide constant current operation.

The combined driver, control circuit and power supply circuitry 28 is electrically connected to an actuator, e.g., an ON/OFF switch or button 30, and is also electrically connected to an indicator lamp 32. The apparatus 20 is configured so that when the ON/OFF switch or button 30 is actuated, e.g., depressed, electrical power is provided from the circuitry 28 to the LED module 26 to energize the LEDs, whereupon the LEDs produce the UVC light. The indicator lamp is coupled to the driver, control circuit and power supply circuitry 28 so that when that circuitry 28 is operating to drive the LEDs, the indicator lamp 32 illuminates to provide a visual indication that the apparatus is "on" and producing the UVC light.

The UVC light guide 24 is best seen in FIGS. 1, 2, 5 and 6 and basically comprises an elongated member which is configured to be inserted within the lumen of the instrument to be sterilized. Thus, the light guide is of sufficiently small external diameter, e.g., in the range of approximately 1 mm to 4 mm to readily fit within the working channel of an endoscope or any other lumen of a medical instrument to be sterilized. The light guide can be flexible or rigid depending upon the application for which it is to be used, although it is generally preferred to be flexible. In any case the light guide has a distal end portion 24A (FIG. 2), a proximal end portion 24B (FIG. 6) and a central longitudinal axis 24C (FIGS. 2 and 6). The proximal end portion 24B of the light guide 24 is configured to be connected to the LED module 26 so that when the UVC light is produced by the LED(s) of that module it enters into the proximal end of the light guide and is internally reflected down the light guide along the axis 24C to the distal end as shown by the broken lines 34 in FIG. 5.

The distal end 24A of the light guide is configured so that the UVC light reaching it is directed radially outward from its distal end portion 24A as shown in FIG. 5. In particular, the distal end of the guide 24 is in the form of a special tip, whose details will be described later, that allows the UVC light to disperse efficiently therefrom to quickly sterilize the immediate area around the tip. It should be pointed out at this juncture, that the term "directed radially outward" as used herein doesn't necessarily mean that the UVC light has to be directed precisely perpendicular to the longitudinal axis in a radial direction, so long as some appreciable portion of the UVC light is directed outward or laterally of the longitudinal axis to quickly sterilize the immediate area around the tip.

The light guide 24 is preferably transparent to UVC light so that it can carry that light through its length from its proximal end 24B to the special tip at the distal end 24C with little or no attenuation or degradation of the germicidal properties of the UVC light produced by the UVC source 26. The light guide can be a single fiber (like shown in FIGS. 2 and 4) or a bundle of plural fibers, or could be a liquid light guide, a holey photonic crystal fiber, a hollow photonic crystal fiber, a large core UV fiber or a UV resistant standard fiber. Moreover, depending upon the construction of the UVC source, e.g., whether or not it includes a single LED or multiple LEDs, and the construction of the light guide, e.g., whether it is in the form of a single optic fiber or plural optic fibers, etc., a coupling component (not shown) may be used to connect the LED(s) of the light source 26 to the proximal end 24B of the light guide to enable the UVC light to be introduced into the light guide with little or no attenuation or degradation.

Turning now to FIGS. 2, 3 and 5 the details of the special tip forming the distal end 24A of the light guide will now be described. To that end, as can be seen the tip of the light guide is in the form of a reflective attachment 36. The attachment 36 basically comprises a sleeve or tube 38 and a reflector member 40. The sleeve or tube is a thin walled member formed of a material, e.g., fused silica or sapphire or any other material which is transparent to UVC light, so that the UVC light which is brought to it can be transmitted therethrough with little or no attenuation or degradation. The sleeve or tube 38 is fixedly secured by joint 42 to the distal end of the light guide 24 as best seen in FIG. 2. In addition to holding the reflector member 40 in place, the sleeve or tube 38 also serves to prevent contamination of the light guide.

The reflector member 40 comprises a body of any suitable material, e.g., plastic, glass, metal, etc., which is fixedly secured within the distal end portion of the sleeve or tube 38. The reflector member 40 includes at least one reflective surface 44 or facet lying in a plane extending at an angle to the longitudinal central axis 24C. In the exemplary embodiment shown the body is generally of a pyramidal shape having four facets 44, each of which forms a respective reflective surface and which extend at an acute angle to the central longitudinal axis. The apex of the pyramidal shaped reflector member 40 is located on the central longitudinal axis and faces in the proximal direction, i.e., towards the light guide 24. The reflective surface of each facet 44 of the reflector member 40 is formed by a metal, e.g., aluminum, or other reflective coating or layer 46. It should be noted at this juncture that the body making up the reflector member 40 may be formed of a material which itself is reflective, in which case a reflective coating or layer may not be needed. Moreover, the body making up the reflective member may be hollow and formed of a transparent material with a reflective coating on the inner surface thereof, so long as it results in a member having at least one reflective surface extending at an angle to the longitudinal axis so that UVC light brought to it is directed radially outward.

It should be pointed out at this juncture that the body making up the reflective member need not be pyramidal shaped, but can be of any shape, e.g., circular, polygon or irregular shape, providing it has at least one surface extending at an angle to the central longitudinal axis so that light brought to that surface is reflected or otherwise directed radially outward. As such, when UVC light is brought to the reflector member 40 by the light guide 24, the light exiting the distal end of the light guide bounces off of the at least one angled surface(s) or facet(s) 44 from whence it passes radially outward through the tube or sleeve 38 to impinge the internal surface of the working channel or lumen to be sterilized as shown in FIG. 5. Thus, any bacteria on that surface will be exposed to a lethal dose of the UVC light.

The method of sterilizing the working channel or lumen 10A of the endoscope 10 will now be described. To that end, the distal end portion 24C of the light guide 24 is introduced into the proximal end of the lumen to be sterilized, e.g., the working channel 10A of endoscope 10. The ON/OFF actuator 30 is depressed to cause the UVC source 26 to produce the UVC light, which then passes through the light guide 24 in the manner as discussed above to impinge the internal surface of the working channel 10A contiguous with the distal end of the light guide and thereby sterilize that surface. In order to sterilize the entire length of the working channel, the light guide is advanced down that channel while the UVC source is activated to thereby sweep the length of the channel with the UVC light, thereby sterilizing the entire length of the channel. Once the entire length of the lumen of the instrument to be sterilized has been exposed to the UVC light emanating from the distal end of the light guide, the light guide can be removed, i.e., retracted out of the instrument's lumen. It should be noted that the UVC light may be left on as the light guide is retracted out of the instrument's lumen, if desired.

As should be appreciated by those skilled in the art, inasmuch as the LEDs for producing the UVC light are located within the housing 22 and hence not within the lumen 10A to be sterilized (which is quite small, e.g., approximately 1.1 mm), they can much larger in size than those which would be located within the lumen to be sterilized, e.g., the LEDs of the Deal et al. device. As such the LEDs used in the subject invention can produce much higher levels of UVC light than the Deal et al. device. Thus, the apparatus of the subject invention can sterilize the lumen of an endoscope or other instrument quickly and easily. Moreover, the apparatus of this invention is quite simple in construction, so that it should be a low cost means for viably sterilizing lumens in medical instruments.

Without further elaboration the foregoing will so fully illustrate our invention that others may, by applying current or future knowledge, adopt the same for use under various conditions of service.

We claim:

1. Apparatus for sterilizing an internal surface of a lumen in a medical instrument, said apparatus comprising:
   an elongated UVC light guide having a central longitudinal axis, said UVC light guide being configured to be extended down the lumen in the instrument and including a distal end portion and a proximal end portion, said proximal end portion being configured to be coupled to a source of UVC light suitable for sterilizing the internal surface of the lumen, the UVC light source including at least one LED for producing UVC light when the at least one LED is energized, whereupon the UVC light is carried internally by said UVC light guide from the source of UVC light to said distal end portion of said UVC light guide; and
   a reflective attachment comprising a sleeve or tube and at least one reflective surface, said sleeve or tube being secured to said distal end portion of said UVC light guide and being formed of a material through which UVC light can readily pass, said at least one reflective surface being located within said sleeve or tube and extending at an angle to said central longitudinal axis and being configured to direct said UVC light radially outward from said central longitudinal axis through said sleeve or tube, whereupon when said UVC light guide is extended into the lumen in the medical instrument the radially directed UVC light passing through said sleeve or tube impinges the internal surface of the lumen to sterilize it.

2. The apparatus of claim 1 wherein said reflective attachment comprises plural reflective surfaces, each of said reflective surfaces extending at an angle to said central longitudinal axis, but facing in a different radial direction with respect to said central longitudinal axis.

3. The apparatus of claim 2 wherein said plural reflective surfaces comprise respective facets of a body formed of a material which is itself reflective of UVC light or which is coated with a material which is reflective of UVC light.

4. The apparatus of claim 2 wherein said UVC light guide comprises an optic fiber.

5. The apparatus of claim 4 wherein said optic fiber comprises a single optic fiber.

6. The apparatus of claim 4 wherein UVC light guide comprises an optic fiber bundle.

7. The apparatus of claim 2 wherein said UVC light guide comprises a liquid light guide.

8. The apparatus of claim 2 wherein said UVC light guide comprises a holey photonic crystal fiber.

9. The apparatus of claim 2 wherein said UVC light guide comprises a hollow photonic crystal fiber.

10. The apparatus of claim 1 wherein said sleeve or tube comprises fused silica or sapphire.

11. The apparatus of claim 1 wherein said apparatus additionally comprises said source of UVC light.

12. The apparatus of claim 1 wherein said source of UVC light located within a housing and wherein said housing includes a switch to control the operation of said source of UVC light and an indicator to indicate when said source of UVC light is providing said UVC light into said fiber optic.

13. The apparatus of claim 1 wherein said UVC light guide comprises an optic fiber.

14. The apparatus of claim 13 wherein said optic fiber comprises a single optic fiber.

15. The apparatus of claim 13 wherein UVC light guide comprises an optic fiber bundle.

16. The apparatus of claim 1 wherein said UVC light guide comprises a liquid light guide.

17. The apparatus of claim 1 wherein said UVC light guide comprises a holey photonic crystal fiber.

18. The apparatus of claim 1 wherein said UVC light guide comprises a hollow photonic crystal fiber.

19. A method of sterilizing an internal surface of a lumen in a medical instrument comprising:
    a) providing an apparatus including an elongated UVC light guide having a central longitudinal axis, a distal end portion and a proximal end portion, said distal end portion including a reflective attachment comprising a sleeve or tube and at least one reflective surface, said sleeve or tube being secured to said distal end portion of said UVC light guide and being formed of a material through which UVC light can readily pass, said at least one reflective surface being located within said sleeve or tube and extending at an angle to said central longitudinal axis and being configured for directing UVC light radially outward from said central longitudinal axis through said sleeve or tube;
    b) coupling a source of UVC light to said proximal end portion of said elongated UVC light guide, said source of UVC light including at least one LED for producing UVC light when said at least one LED is energized;
    c) inserting said UVC light guide within said lumen of said instrument;
    d) energizing said source of UVC light to produce UVC light, whereupon said UVC light guide carries said UVC light from said source of UVC light internally down said UVC light guide to said reflective attachment from whence said UVC light is directed radially outward through said sleeve or tube to impinge said internal surface of said lumen to sterilize that surface; and
    e) moving said UVC light guide through said lumen while said source of UVC light is producing said UVC light to thereby sterilize the length of said internal surface of said lumen.

20. The method of claim 19 wherein said UVC light guide comprises an optic fiber.

21. The method of claim 20 wherein said optic fiber comprises a single optic fiber.

22. The method of claim 20 wherein UVC light guide comprises an optic fiber bundle.

23. The method of claim 19 wherein said UVC light guide comprises a liquid light guide.

24. The method of claim 19 wherein said UVC light guide comprises a holey photonic crystal fiber.

25. The method of claim 19 wherein said UVC light guide comprises a hollow photonic crystal fiber.

* * * * *